United States Patent [19]

Yamanobe et al.

[11] Patent Number: 5,196,873
[45] Date of Patent: Mar. 23, 1993

[54] EYE MOVEMENT ANALYSIS SYSTEM

[75] Inventors: Shigeharu Yamanobe, Nagasaki; Norio Ishikawa, Tokyo, both of Japan

[73] Assignees: Nihon Kohden Corporation; Toshiaki Yagi, Tokyo, Japan

[21] Appl. No.: 693,196

[22] Filed: Apr. 30, 1991

[30] Foreign Application Priority Data

May 8, 1990 [JP] Japan .................. 2-116943

[51] Int. Cl.$^5$ ............................... A61B 3/14
[52] U.S. Cl. ................................ 351/210
[58] Field of Search ................ 351/209, 210, 211

[56] References Cited

U.S. PATENT DOCUMENTS 4,702,575 10/1987 Breglia .

FOREIGN PATENT DOCUMENTS 0346846 12/1989 European Pat. Off. .
2207748 4/1988 United Kingdom .
8806859 9/1988 World Int. Prop. O. .

OTHER PUBLICATIONS

"Eye Movement Analysis System Using Computerized Image Recognition", The Archives of Otolaryngology–Head & Neck Surgery, Mar. 1990, vol. 116, pp. 338-341.

Primary Examiner—Rodney B. Bovernick
Attorney, Agent, or Firm—Sughrue, Mion, Zinn, Macpeak & Seas

[57] ABSTRACT

An eye movement analysis system projects imaging light to an eyeball for a time duration short enough so as not to create blurring. Image data is then recorded onto a recording medium. The image data is then read out of the recording medium and used to calculate positional data concerning the eyeball's present location. At a later time, image data of the eyeball is again recorded in the recording medium and read out to calculate positional data concerning the eyeball's new location. The two sets of positional data are used to calculate eye movement data for use in diagnosing the causes of vertigo and/or disequilibrium.

7 Claims, 10 Drawing Sheets

1/60 SEC. ELECTRONIC SHUTTERING

FIG. 6(b)

SHUTTER OPEN
SHUTTER CLOSE

1/1000 SEC. FLASH LIGHT BEAMS

EYE MOVEMENT ANALYSIS SYSTEM

FIELD OF THE INVENTION

This invention relates to an eye movement analysis system for measuring and analyzing eye movements including a torsional component of eye movement, for use e.g., when diagnosing the causes of vertigo and/or disequilibrium.

BACKGROUND OF THE INVENTION

For diagnosis of patients with vertigo and/or disequilibrium, it is important to analyze eye movements in terms not only of the horizontal and vertical components but also of the torsional component as well. However, generally practiced electronystagmography (ENG) permits analyses of only the horizontal and vertical components of eye movements.

Other conventional methods of measuring eye movements include high-velocity photography and video monitoring. The high-velocity photography method takes pictures of iris striations (positions of the eyeball not at the eyeball center) of an eyeball using a high-velocity camera, develops the pictures, and then sequentially measures striation movements relative to the center of a pupil by applying a scale to each printed picture, so that the torsional angle and velocity of the eyeball are calculated.

The video monitoring method, on the other hand, reproduces iris striation movements imaged by a video camera on a monitoring unit, sequentially measures the movement of striations relative to the center of a pupil by applying a scale on the monitoring unit on a single field or frame basis, so that the torsional angle and velocity of the eyeball are calculated.

Also known is a method of measuring the torsional component of eye movements by tracing an eyeground pattern, instead of tracing the movement of iris striations, using the high-velocity photography and the video monitoring method.

The high-velocity photography method requires that after having taken pictures, the film be developed and printed, thereby entailing much time and labor. Also, a cumbersome operation of applying a scale to each printed picture must be undergone.

The video monitoring method also requires that eye movements be measured by applying a scale to each image visualized on the monitoring unit and then calculated, thereby being time-consuming in measurement as in the high-velocity photography.

Thus, neither the high-velocity photography nor the video monitoring method can produce measurement results quickly, and it is for this reason that they have not been suitable for clinical applications.

In the technique for measuring eye movements by tracing an eyeground pattern, movement of the center of the pupil or contraction of the pupil hides and blinds the eyeground pattern. Thus, this technique is more difficult compared to the techniques for tracing the iris striations.

SUMMARY OF THE INVENTION

The invention has been proposed to overcome the above problems. Accordingly, an object of the invention is to provide an eye movement analyzing system adapted for use in clinical applications which is capable of significantly reducing eye movement measuring time.

To achieve the above object, a first aspect of the invention is applied to an eye movement analysis system which comprises: imaging means including an imaging camera and a light source for projecting imaging light to an eyeball to image eye movements through such a quick exposure as not to blur the imaging object; image recording means for recording imaged outputs produced from the imaging camera of the imaging means every single piece of image data; tracing a target specifying means for specifying the center of an eyeball and a position outside the center of the eyeball, the center of the eyeball and the position outside the center of the eyeball being designations for tracing imaged outputs produced from the imaging camera or data read from the imaging recording means; position coordinate calculating means for calculating position coordinates of the center of the eyeball and the position outside the center of the eyeball specified by the tracing a target specifying means for each piece of image data sequentially read from the image recording means; and eye movement calculating means for calculating an eye movement incorporating a torsional component from time-dependent changes in the position coordinates of the center of the eyeball and position outside the center of the eyeball obtained from the position coordinate calculating means.

A second aspect of the invention is applied to an eye movement analysis system, in which polarizing plates are disposed in front of an optical lens of the imaging camera and in front of the light source to reduce the influence of light reflected from the surface of an eyeball, the polarizing plates having polarizing angles which are different from each other.

A third aspect of the invention is applied to an eye movement analysis system, in which polarizing plates are disposed in front of an optical lens of the imaging camera and in front of the light source, and quarter-wave plate are disposed in front of the polarizing plates.

A fourth aspect of the invention is applied to an eye movement analysis system, in which a light-transmitting light-scattering member (diffuser) is disposed in front of the light source.

A fifth aspect of the invention is applied to an eye movement analysis system, in which the light source is oriented opposite to an eyeball; a light reflecting board is disposed so as to confront the light source; and a cylindrical light reflecting board is disposed around the light source.

A sixth aspect of the invention is applied to an eye movement analysis system, in which a light-emitting diode is used as the light source, and when lighting the light-emitting diode for a short duration to perform the quick exposure, the light-emitting diode is reverse-biased or the anode of the light-emitting diode is grounded in synchronism with a fall of a light-emitting pulse signal supplied to the light-emitting diode.

According to the first aspect of the invention, the time-dependent changes in the position coordinates of the center of the eyeball and position outside the center of the eyeball are sequentially calculated for each single frame of image data of the eye movement imaged by such quick exposure as not to blur the imaging object, thereby allowing the eye movements including the torsional component to be measured highly accurately. The quick exposure can be implemented by a high-velocity shuttering or a short irradiation of flash light beams.

According to the second aspect of the invention, the light from the light source is polarized by the polarizing plate disposed in front of the light source to reach the eyeball surface and further polarized when reflected by the eyeball surface. Therefore, as long as a separate polarizing plate whose polarizing angle is different from the polarizing plate in front of the light source is arranged in front of the optical lens section so that the reflected light can be shielded, the reflected light from the eyeball surface no longer penetrates into the optical lens section directly.

According to the third aspect of the invention, quarter-wave plates are respectively arranged in front of the deflection filters. Therefore, the linearly polarized light passing through the polarizing plates can be converted into circularly polarized light, thereby reducing penetration of the reflected light to the optical lens section without adjusting the angles of the two polarizing plates.

According to the fourth aspect of the invention, the light-transmitting light-scattering member (diffuser) is arranged in front of the light source, thereby shutting direct entry of light into the optical lens section and thus reducing influence of the reflected light from the eyeball surface.

According to the fifth aspect of the invention, it is the indirect light, not the direct light, that is projected into the eyeball, thereby reducing influence of the reflected light from the eyeball.

According to the sixth aspect of the invention, the electric charges still remaining at floating capacitors after input stoppage can be released, thereby causing the light-emitting diode to fall steeply during its transition from conduction to nonconduction. Thus, flash light beams injected by a sharp irradiation pulse can be irradiated to the eyeball.

BRIEF DESCRIPTION OF THE DRAWINGS

FIGS. 6 (a) to (c) are waveform charts illustrating an operation of the eye movement analysis system;

FIGS. 7 (a) and (b) are diagrams respectively showing an eyeball with a window set to specify tracing a target on the eyeball visualized on a monitoring unit, and a video signal waveform when the eyeball has been imaged;

FIGS. 8 (a) to (c) are diagrams showing measurement results of eye movements obtained using the eye movement analysis system;

FIGS. 9 (a) and (b) are waveform diagrams respectively showing a light-emitting characteristic of an LED used as a light source and a characteristic after the light-emitting characteristic has been improved;

FIGS. 14 (a) to (c) are waveform diagrams illustrating an operation of another exemplary eye movement analysis system of the invention.

DETAILED DESCRIPTION OF THE PREFERRED EMBODIMENTS

Embodiments of the invention will be described in detail with reference to the accompanying drawings.

Figure 1:
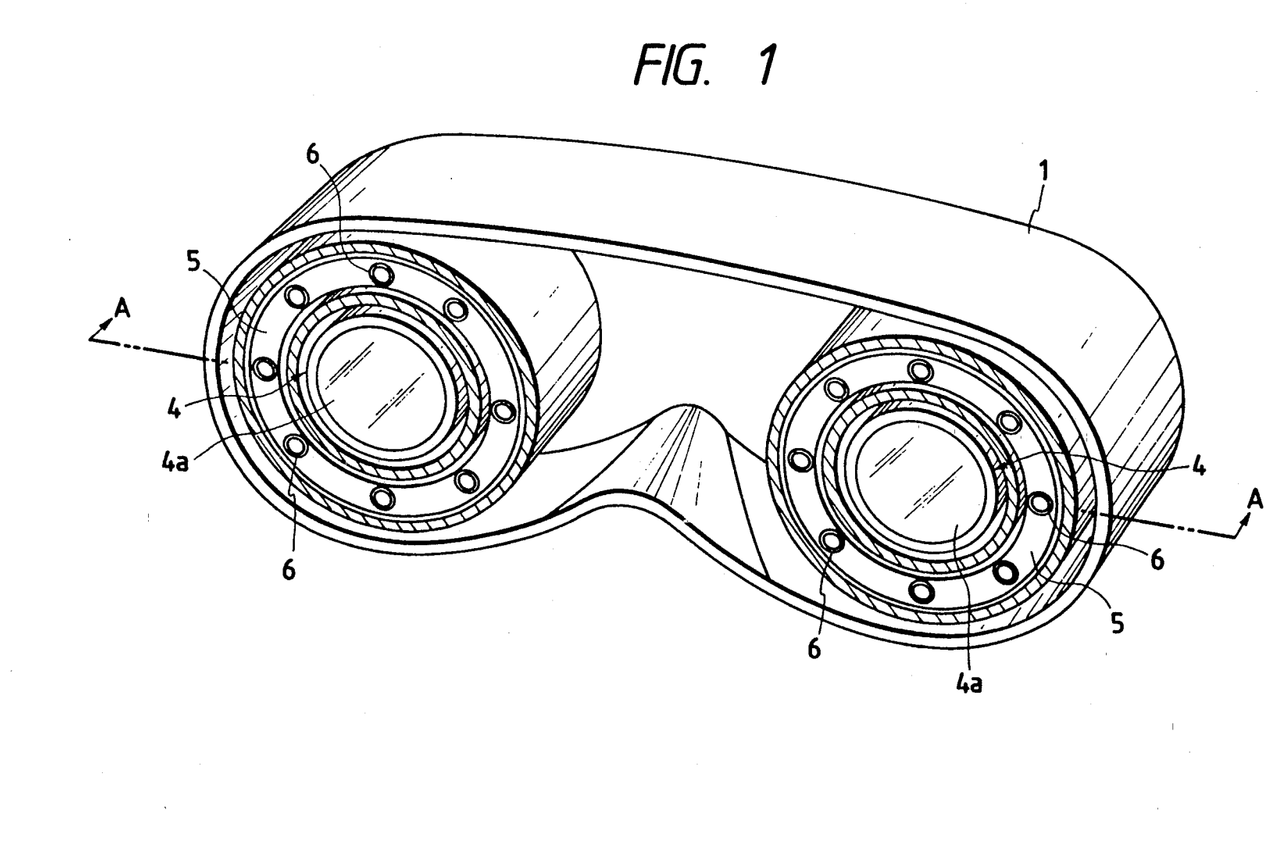
FIG. 1 is a perspective view showing an exemplary pair of goggles to be worn by a subject whose eye movement is measured using an eye movement analysis system of the invention.
Figure 2:
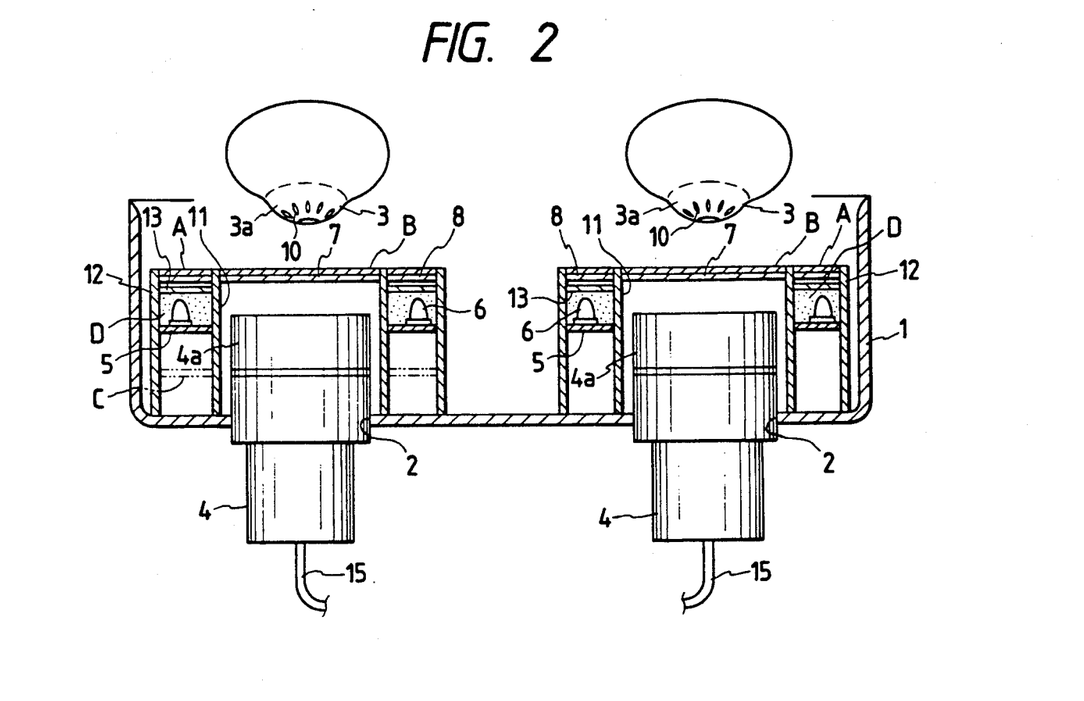
FIG. 2 is a sectional view taken along a line A—A shown in FIG. 1.

FIG. 1 is an embodiment of a pair of goggles to be attached to the face of a subject when his or her eye movements are to be measured using an eye movement analysis system of the invention. FIG. 2 is a sectional view taken along a line A—A shown in FIG. 1.

In FIG. 2, to attachment holes 2 bored in a front portion of a goggles body 1 are video cameras 4 attached to image the right and left eyeballs 3 of the subject. Each video camera 4 is arranged so that an extension of its optical axis positions the center of an eyeball. Charge-coupled devices (CCDs) are used as these video cameras 4.

Around an optical lens section 4a of each video camera 4 within the goggles body 1 are a plurality of light sources 6, which are mounted on a ring-like board 5. Each light source 6 projects flash light beams to the eyeballs 3 of the subject at the time the eyeballs are being imaged. In this embodiment, infrared LEDs (light-emitting diodes) are used as these light sources 6.

Figure 7A:
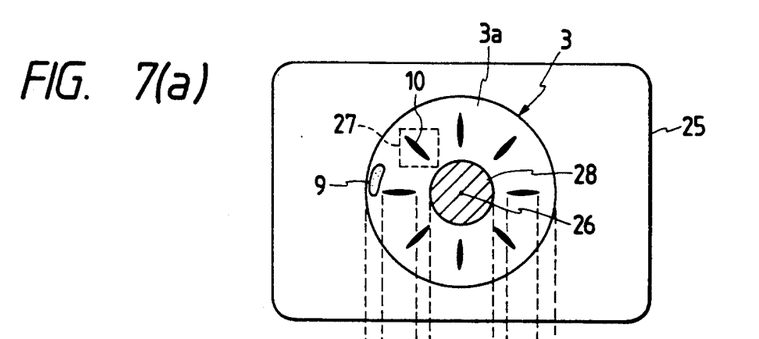

Polarizing plates 7, 8 are disposed in front of the optical lens section 4a and the light sources 6, respectively, and the polarizing plates have polarizing angles which are different form each other, so as to prevent disturbance with imaging of iris striations 10 by light reflection 9 from each eyeball surface 3a (see FIG. 7).

Further, quarter-wave plate A, B are provided in front of the respective polarizing plates 7, 8. The arrangement of the quarter-wave plates A, B causes any linearly polarized light beams which have passed the polarizing plates 7, 8 to be converted into circularly polarized light beams, thereby allowing the influence from the light reflection 9 to be alleviated without finely adjusting the angles of the polarizing plates 7, 8.

As shown in FIG. 2, between each optical lens section 4a and the corresponding light sources is a cylindrical shielding board or cylindrical light-scattering board 11 (diffuser) provided to prevent direct leakage of the light emitted from the respective light sources 6 toward the corresponding camera 4. A cylindrical light reflecting board 12 arranged around the corresponding light sources 6 serves to effectively guide the light from the light sources 6 toward the corresponding eyeball 3.

Each light source 6 may be oriented opposite to the eyeball 3 instead of facing the eyeball 3, and a light reflecting board C may be introduced so that indirect light beams reflected by the light reflecting board C may be projected onto the eyeball 3.

Figure 3:
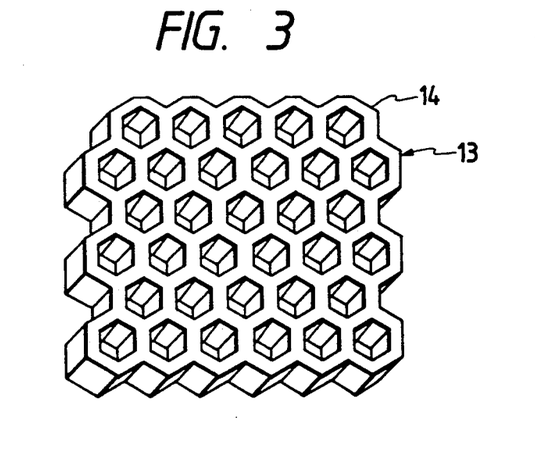
FIG. 3 is a perspective view showing an exemplary light-scattering board (diffuser) used in the pair of goggles.

Between each light source 6 and its corresponding polarizing plate 8 is a light-transmitting light-scattering board (diffuser) 13. The light beams from each light source 6 are first scattered by the light-scattering board (diffuser) 13 and then projected onto the eyeball 3, thereby allowing the light reflection 9 from the eyeball surface 3a to be reduced. A honeycomb board 14 such as shown in FIG. 3, a milky board, or thin paper or woven fabric may be used as the light-scattering board (diffuser) 13.

In this embodiment a light-transmitting light-scattering resin D is charged around each light source 6 and hardened, thereby making it further advantageous in reducing the light reflection 9 from the eyeball surface 3a. An arrangement employing either the light-scattering board (diffuser) 13 or the light-transmitting light-scattering resin D may also be applicable.

A construction of the eye movement analysis system and its operation will be described with reference to a block diagram shown in FIG. 4 and a flow chart shown in FIG. 5. The eye movement analysis system serves to measure eye movements by processing images photographed by the video cameras 4 and to control the light sources 6 for emitting flash light beams.

Figure 4:
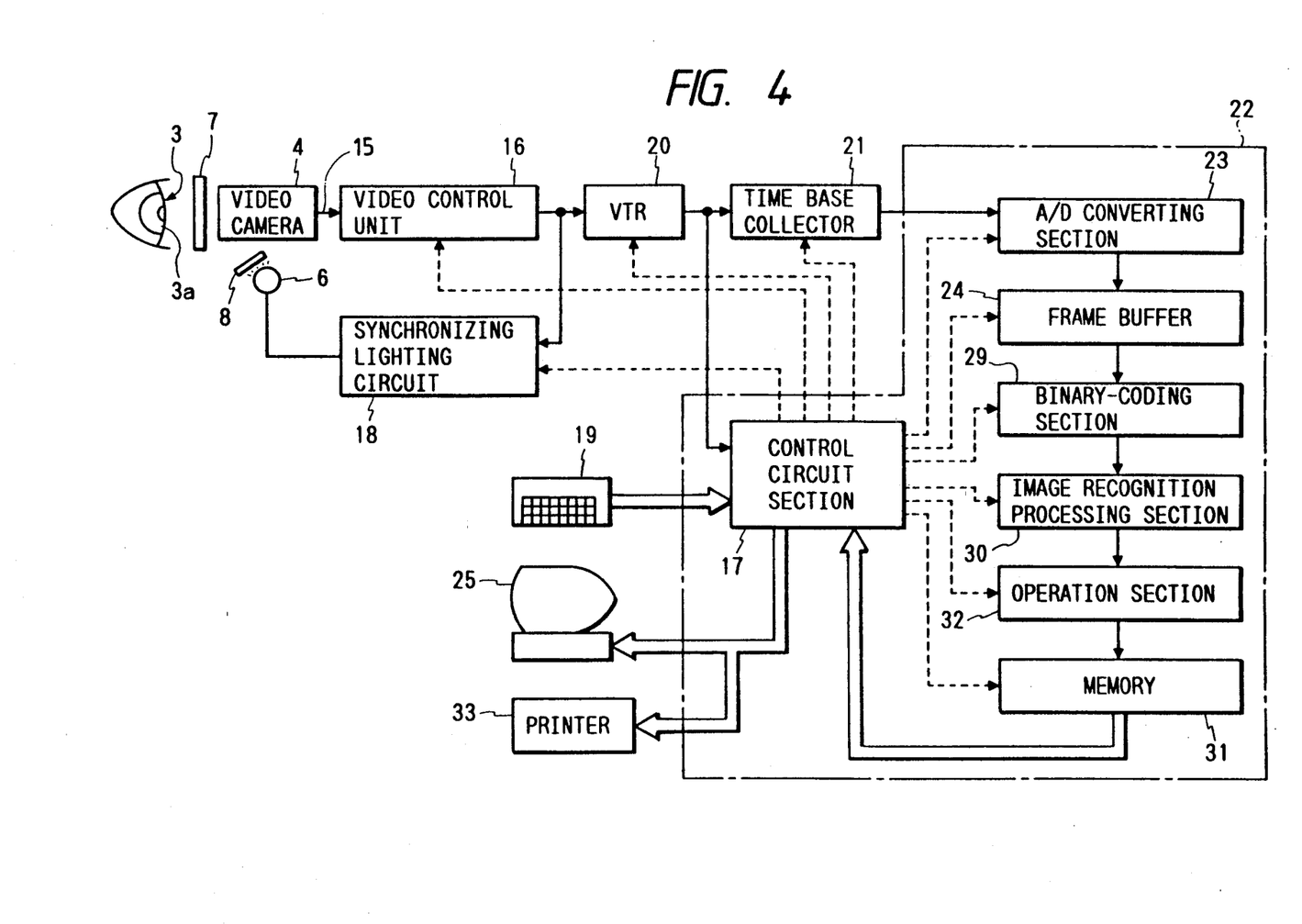
FIG. 4 is a block diagram showing an exemplary eye movement analysis system of the invention.
Figure 5A:
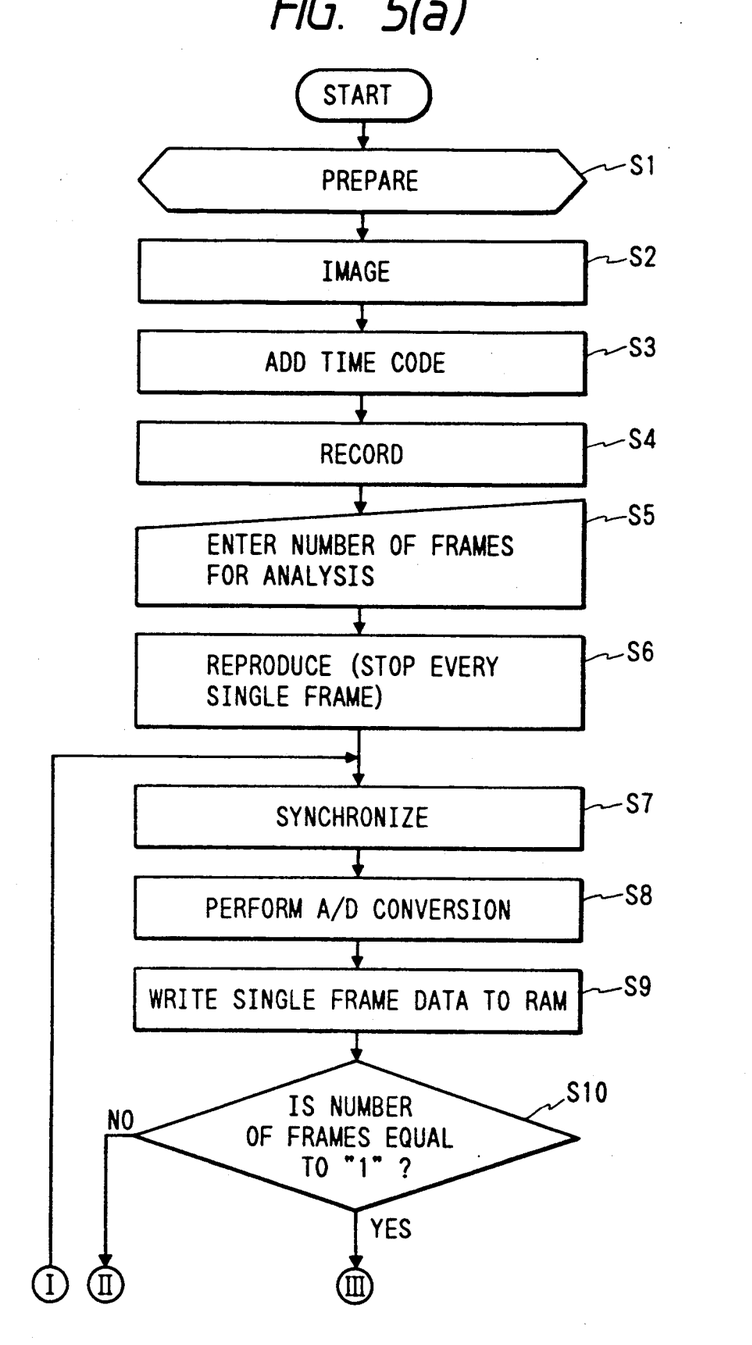
FIGS. 5A and 5B are a flow chart showing an operation of the eye movement analysis system.
Figure 5B:
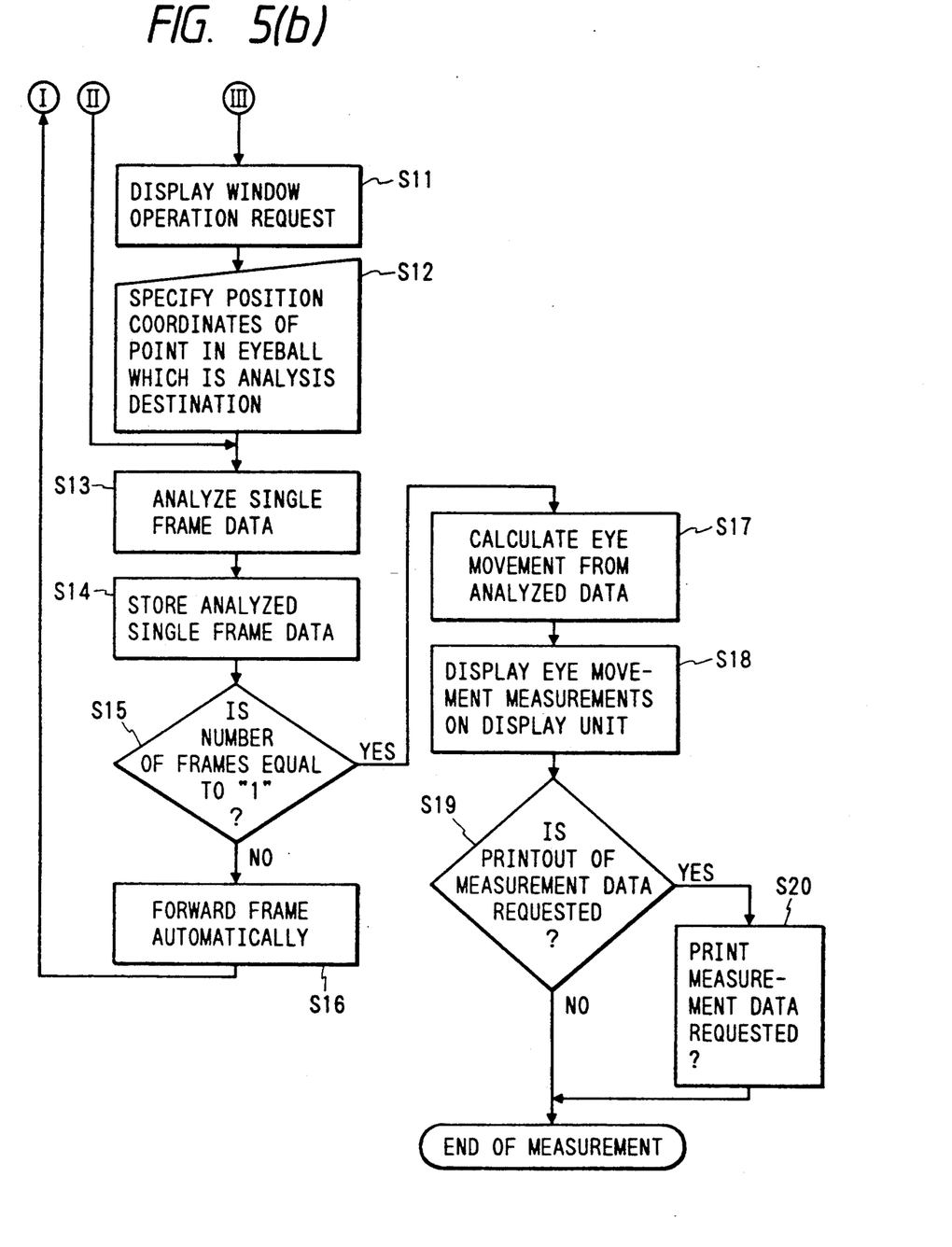
Figure 6A:
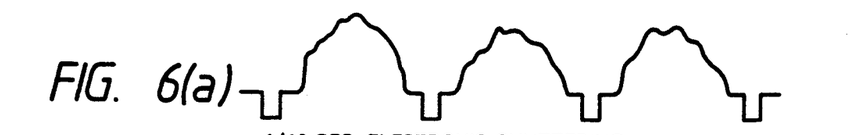
Figure 6B:
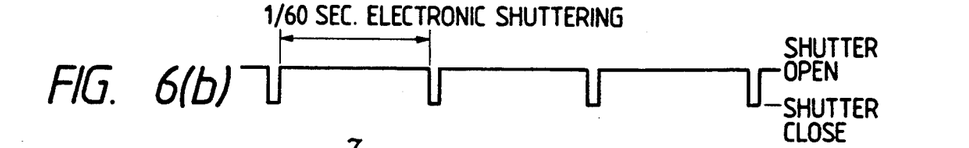

In FIGS. 4 and 5, the respective video cameras 4 in the goggles body 1 are connected to a video camera control unit 16 through cables 15, and an electronic shutter speed of these video cameras 4 is set by the video camera control unit 16 that is controlled by a control circuit section 17. The electronic shutter speed is usually set to 1/60 second by means of keyboard 19. FIG. 6 (b) shows shutter opening and closure timings, while FIG. 6 (a) shows a waveform of a video signal outputted from the video control unit 16.

Figure 6C:
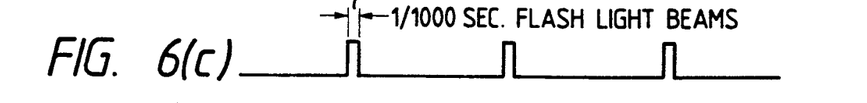

A composite video signal outputted from the control unit 16 is supplied to a synchronizing lighting circuit 18. This circuit 18 controls the light sources 6, so that each light source 6 is turned on at a cycle of 1/60 second, which is in synchronism with the output of each video signal. In this embodiment, the lighting time of each light source 6 is set to, e.g., in the order of 1/300 to 1/1000 second, which is a time not blurring the imaging object when the movement of iris striations 10 is being imaged. Although the lighting output from the light source 6 must be increased in inverse proportion to its irradiation time for clear imaging, too large a lighting output may be harmful to the eyeballs. Thus, the irradiation time duration τ is to be set to so small a value that the eyeballs can be safeguarded from the stored energy from the irradiation of light. An upper limit of the stored energy which is not detrimental to the human body is generally considered to be 1 mW/m². As shown in FIG. 6 (c), the irradiation time duration τ is set to 1/1000 second in this embodiment.

The video cameras 4, the camera control unit 16, the light sources 6, and the synchronizing lighting circuit 18 constitute imaging means for imaging eye movements by such quick exposure as not to blur an imaging object.

In the flow chart, the preparation in Step S1 corresponds to causing the subject to wear the goggles and having a shutter speed and an irradiation time duration τ of each light source 6 set from a keyboard 19.

When the subject has worn the goggles and eye movements of the eyeballs of the subject have been imaged by the video cameras 4, imaged data signals from the video cameras 4 are fed to a VTR (video tape recorder) 20 through the video camera control unit 16 and recorded. The VTR 20 is a video recording means. A time code is appended to each video signal recorded at this time. This time code helps in searching target image data. These processes correspond to Steps S2 to S4.

In Steps S5, a desired number of frames (n) to be analyzed is entered from the keyboard 19. The number of frames (n) is set to, e.g., in the order of 30.

Then, upon start of reproduction (playback) by the VTR 20, reproduction output signals are fed to a time base collector 21, where the operation of matching a synchronizing signal at the VTR 20 and an image synchronizing signal at an image processor 22 is performed. The VTR 20 maintains the reproduction (playback) signal of a first frame until a frame forwarding signal is supplied from the control circuit section 17. The processes up to this point correspond to Steps S6 and S7.

The video signal being through with the time base collector 21 is then supplied to an A/D converter 23 of the image processor 22 and converted into a digital signal. The data equivalent to a single frame are stored in a frame buffer (RAM) 24 (steps S8 and S9).

Figure 7B:
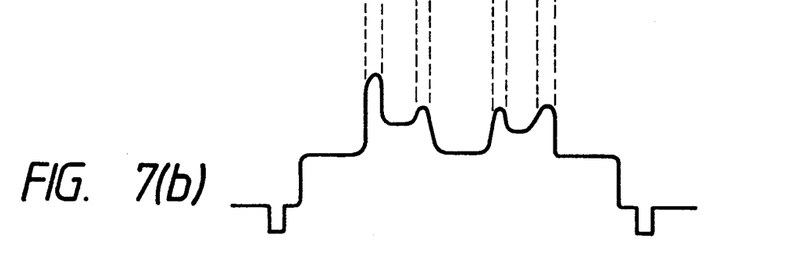

Successively, as shown in FIG. 7 (a), to locate the center of each eyeball of the subject and desired iris striations while viewing a reproduced (played) image on the screen of a display 25, the operation of setting a window 27 to each eyeball center and the corresponding striation (the position outside the eyeball center) is performed (Steps S10 and S12). This operation may be performed only for the first frame. FIG. 7 (b) shows a variation of signal levels of a pupil 28 and iris striations 10 appearing in the video signal. The control circuit section 17 and the display 25 constitute tracing destination specifying means.

Then, the data read from the frame buffer 24 are fed to a binary-coding section 29 and converted into two kinds of image data (luminance data) corresponding to a light level and a dark level. The binary boding allows easy processing of an image recognition processing section 30.

Light and dark points are recognized at the image recognition processing section 30 to which binary-coded data is sent from the binary-coding section 29. As a result of such recognition processing, each eyeball center 26 and iris striations 10 located by the window setting operation can be traced, and the operation of determining the position coordinates of the eyeball center 26 and iris striations 10 is performed. The respective position coordinates obtained by the analysis are stored in a memory 31 (Steps S13 and S14). The image recognition processing section 30 constitutes position coordinate calculating means.

Then, the frame forward operation is performed automatically by the VTR 20 to reproduce video signals for a second frame, and the reproduced data are analyzed based on the above-described processing. As a result, the position coordinates of the eyeball center 26 and iris striations 10 which have moved are calculated. These operations correspond to Steps S15 and S16, S7 to S10, S13, and S14.

Figures 8A, 8B, 8C:
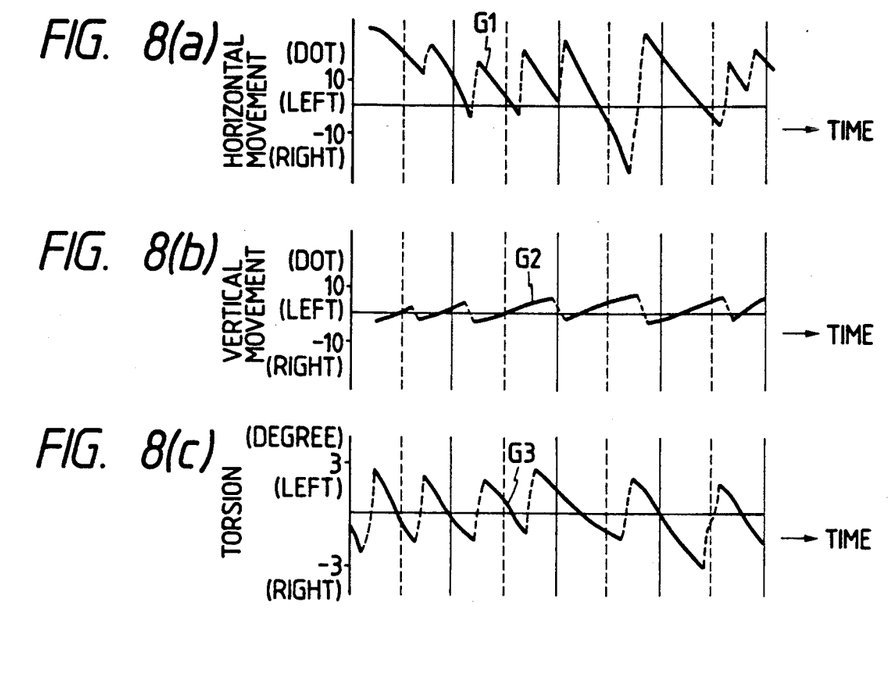

The same operations are repeated thereafter up to an Nth frame (the 30th frame in this embodiment) so that the operation of analyzing and determining the position coordinates of the eyeball centers and positions outside the eyeball centers will be completed (Step S15). Then, the operation of calculating time-dependent vertical and horizontal changes (movements) as well as time-dependent torsional angle changes in the position coordinates of the eyeball center 26 and iris striations 10 (the positions outside the eyeball center) from the respective analyzed data is performed at an operation section 32 that constitutes eye movement calculating means. The operation results are stored in an area in memory 31, while displayed on the display 25 (Steps S17 and S18). FIG. 8 shows graphs (G1, G2, G3) showing measurement results. FIG. 8 (a), or G1, shows a horizontal movement component of the eyeball 3; FIG. 8 (b), or G2, shows a vertical movement component; and FIG. 8 (c), or G3, shows a torsional component of the eyeball 3.

Upon instruction for a printout from the keyboard 19, hard copies of the measurement results are made by a printer 33 (Steps S19 and S20).

Exemplary configurations of the synchronizing lighting circuit 18 will be described next. This circuit 18 serves to turn on each light source 6 so that a steeply falling irradiation pulse is emitted from the light source made up of an LED.

Figures 9A, 9B:
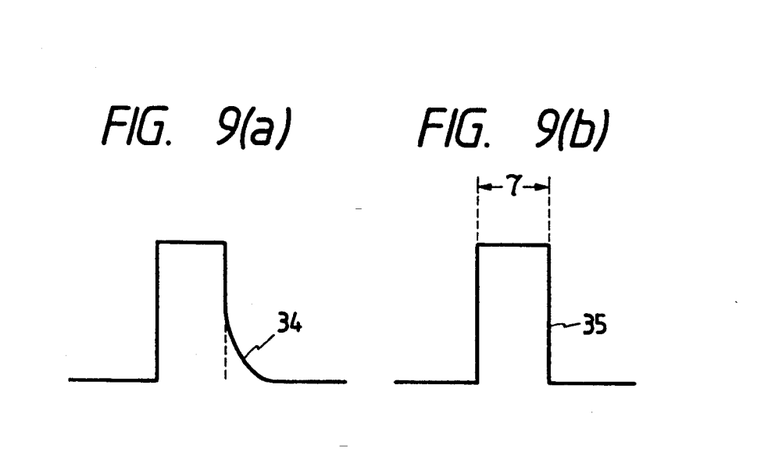

Even through a rectangular pulse is received, the generally poor frequency characteristic of the LED causes a rounding 34 in the falling edge of an emitted light pulse as shown in FIG. 9 (a). To eliminate the rounding 34 in the falling edge and obtain a steeply falling irradiation pulse 35 at an irradiation time duration $\tau$ as shown in FIG. 9 (b), electric charges remaining at floating capacitors and the like after the stoppage of an input may be discharged in some way.

Figure 10:
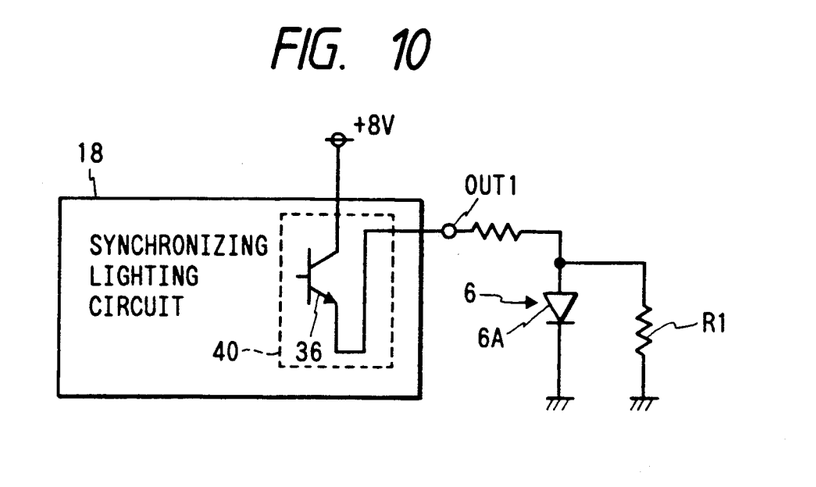
FIG. 10 is a circuit diagram showing an exemplary lighting circuit for improving the light-emitting characteristic of the LED.

In an exemplary circuit shown in FIG. 10, a resistor R1 is connected in parallel with an LED 6A, which is a light source 6, to discharge the remaining electric charges.

In FIG. 10, the emitter of an output transistor 36 of the synchronizing lighting circuit 18 is connected to the anode of the LED 6A whose cathode is grounded, and the bypass resistor R1 is connected in parallel to this LED 6A. The base of the output transistor 36 is to receive an LED drive pulse signal having a duration equivalent to the irradiation time duration $\tau$. Since a power source voltage is 8 V in this embodiment, a resistor of 100 kΩ or so may be used as the resistor R1. A steeply falling lighting output can be obtained because the electric charges stored after the input has stopped is shorted to ground by resistor R1.

Figure 11:
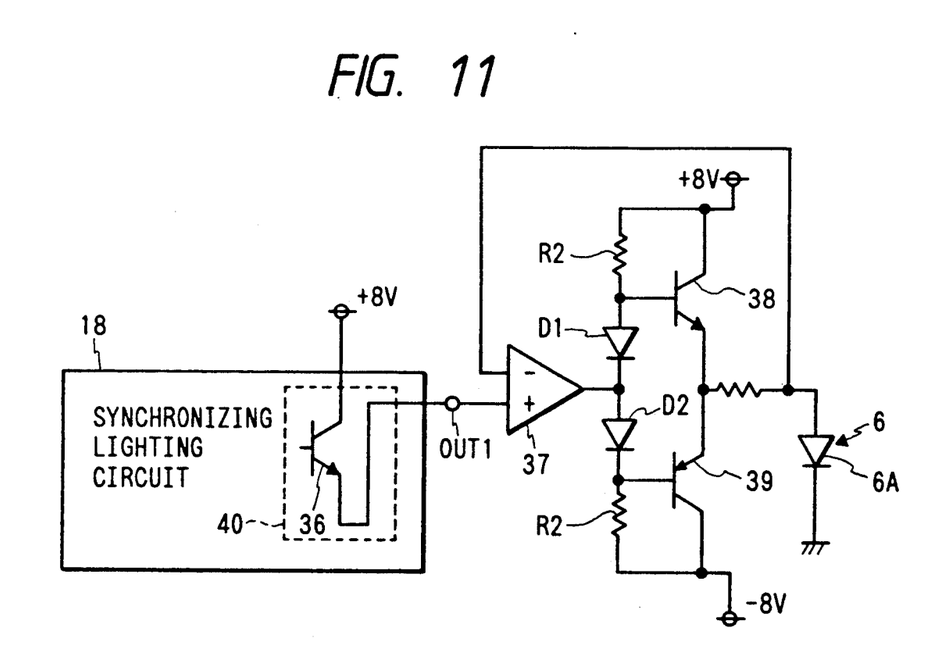
FIG. 11 is a circuit diagram showing another exemplary lighting circuit.

Another exemplary circuit configuration shown in FIG. 11 introduces a differential amplifier 37 and transistors 38 and 39 in Complementary connection to improve the LED 6A characteristic.

In FIG. 11, an output terminal OUT1 of the synchronizing lighting circuit 18 is connected to the noninverting input terminal of the differential amplifier 37, the output terminal of which is connected to the input terminal of the output transistors 38, 39 in complementary connection. The output terminal of the output transistors 38, 39 which are in complementary connection is connected not only to the inverting input terminal of the differential amplifier 37 but also to the anode of the LED 6A whose cathode is grounded. Reference numeral R2 is a bias resistor; and D1, a reverse flow blocking diode.

With this construction, as long as a lighting pulse is being outputted from an output circuit 40 of the synchronizing lighting circuit 18, the output terminal OUT1 of the amplifier 37 remains high, thereby lighting the LED 6A while turning on the transistor 38. However, upon the falling edge of the lighting pulse output, the potential of the inverting input terminal of the differential amplifier 37 exceeds the potential of the noninverting input terminal influenced by the rounding 34 in the falling edge of the LED output. As a result, the output level of the differential amplifier 37 goes low. This causes the transistor 39 to turn on, shorting the anode of the LED 6A to the negative power voltage. This reverse biasing serves to discharge the electric charges stored at the LED 6A, thereby causing the lighting output of the LED 6A to fall steeply.

Figure 12:
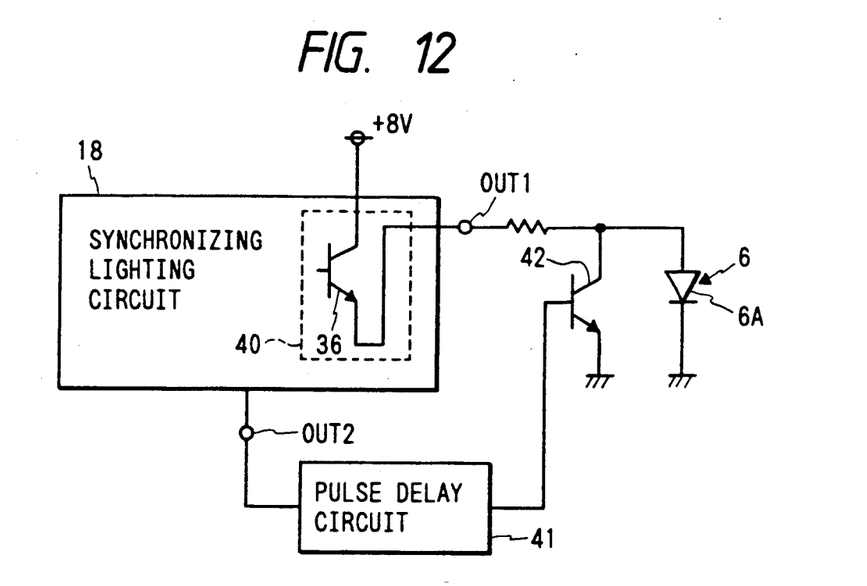
FIG. 12 is still another exemplary lighting circuit.

Still another exemplary circuit configuration using a pulse delay circuit 41 shown in FIG. 12 is possible and will be described next.

In this example, an oscillating output pulse to be supplied to the output circuit 40 of the synchronizing lighting circuit 18 is received from an output terminal OUT2. After having been delayed by a single pulse at a pulse delay circuit 41, this output pulse is applied to the base of a transistor 42 that is inserted between an output terminal OUT1 of the synchronizing lighting circuit 18 and ground.

Accordingly, the anode of the LED 6A connected to the output terminal OUT1 is shorted to ground upon the falling edge of a lighting pulse output and conduction of the transistor 42, allowing the rounding 34 of an LED output to be improved.

Still another exemplary circuit configuration using an inverting circuit 43 and a pulse delay circuit 44 shown in FIG. 13 will be described.

Figure 13:
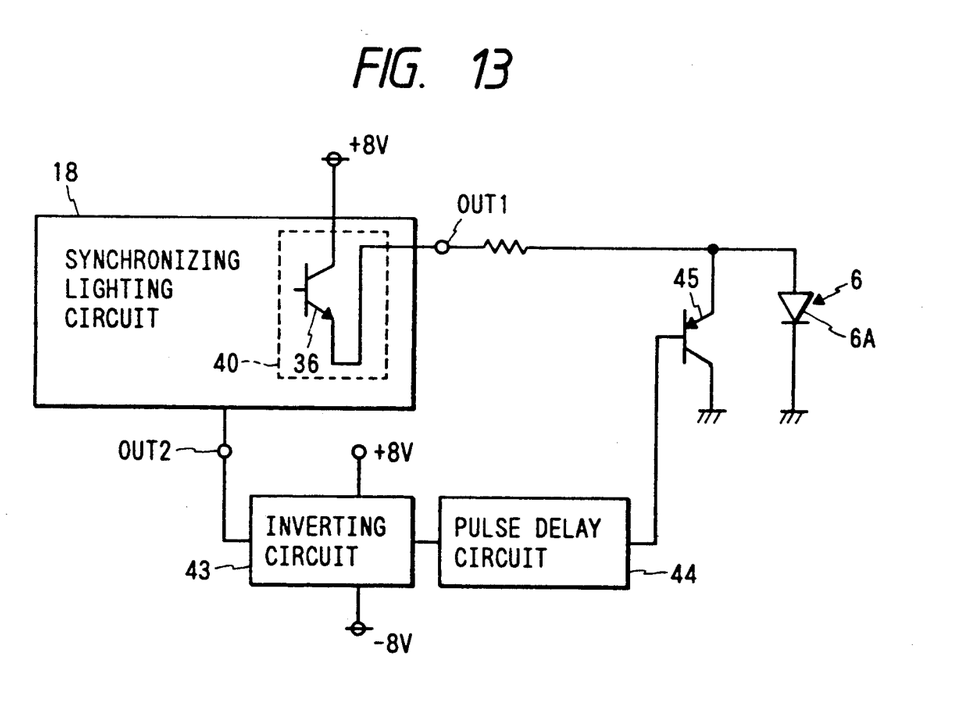
FIG. 13 is a circuit diagram showing still another exemplary lighting circuit.

In FIG. 13, an oscillating output pulse received from an output terminal OUT2 of the synchronizing lighting circuit 18 is inverted at the inverting circuit 43, delayed by a single pulse at the pulse delay circuit 44, and applied to the base of the NPN transistor 45 inserted between an terminal output OUT1 and ground.

Accordingly, upon the falling edge of a lighting pulse output and conduction of the transistor 45 to which the inverted delay output is applied, the anode of the LED 6A is shorted to ground, thereby allowing the lighting output of the LED 6A to fall steeply.

The use of such lighting circuits allows sharp flash light beams to be irradiated onto the eyeballs of subjects, thereby contributing to measurement with improved accuracy.

Figure 14A:
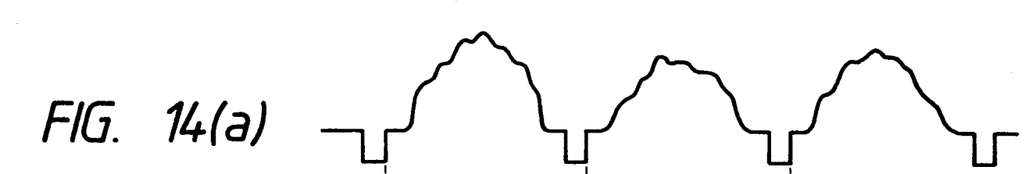
Figures 14B, 14C:
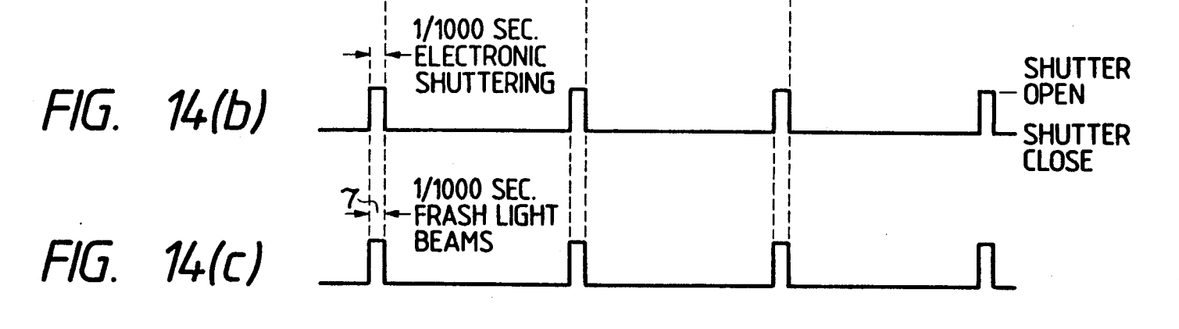

Another embodiment will be described with reference to the waveform diagrams shown in FIGS. 14 (a) to (c).

In this embodiment, the electronic shutter speed is set to 1/1000 second, instead of 1/60 second, and the light sources 6 are turned on at an irradiation time duration $\tau$ of 1/1000 in synchronism with the opening and closing of the electronic shutter.

As a means for implementing such quick exposure as not to blur imaging objects, the electronic shutter speed of each video camera 4 may simply be set to a high speed of, e.g., 1/1000 second, instead of providing flash beams.

If video signals applied from the video control unit 16 are recorded not in the VTR 20, but converted to digital data and recorded in a photoelectromagnetic disk unit or laser disk unit on a single frame basis, then the time base collector 21 and the A/D converting section 23 can be eliminated. Thus, outputs of the photoelectromagnetic disk unit or laser disk unit can be directly supplied to the frame buffer 24.

Further, eye movements may be imaged by a high-speed electronic still camera, instead of the video camera 4, and an imaged data signal from this electronic still camera may be processed so that the eye movements can be measured.

Furthermore, a target outside the eyeball center, which is a tracing destination, may be an eyeground pattern that can be viewed from the pupil 28, instead of iris striations 10.

As described in the foregoing, according to the eye movement analysis system according to the invention, eye movements are measured by irradiating flash light beams with such a short pulse of, e.g., 1/1000 second as to allow quick exposure to the eyeballs of a subject so that the eye movements are imaged and the image signals are analyzed by image recognition processing. Thus, the eye movements can be measured accurately without blurring the imaging objects.

Accordingly, the eye movement analysis system according to the invention is suitable for use as a clinically applicable apparatus that allows, e.g., patients suffering from encephalopathy to be diagnosed based on measurements of eye movements including the torsional component of movement.

In addition, the use of the polarizing plates (quarter-wave plates may be additionally provided) and light-transmitting light-scattering member allows influence of light reflection from the eyeball surfaces to be reduced, thereby contributing to error-free, highly accurate measurement.

The feature of irradiating sharp flash light beams to the eyeballs which permits quick exposure also allows blur-free, highly accurate measurement.

What is claimed is:

1. An eye movement analysis apparatus comprising:
   imaging means including an imaging camera and a light source for projecting imaging light to an eyeball to image eye movements through such a quick exposure as not to blur an imaging object;
   image recording means for recording imaged outputs produced from said imaging camera of said imaging means;
   tracing destination specifying means for specifying the center of an eyeball and a position outside said center of said eyeball, said center to said eyeball and said position outside said center of said eyeball being designations for tracing imaged outputs produced from said imaging camera;
   position coordinate calculating means for calculating position coordinates of said center of said eyeball and said position outside said center of said eyeball specified by said tracing destination specifying means for each single piece of image data sequentially read from said image recording means; and
   eye movement calculating means for calculating an eye movement incorporating a torsional component from time-dependent changes in position coordinates of said center of said eyeball and said position outside said center of said eyeball obtained from said position coordinate calculating means, wherein polarizing plates are disposed in front of an optical lens of said imaging camera and in front of said light source to reduce influence of light reflected from the surface of said eyeball, said polarizing plates having polarizing angles which are different from each other.

2. An eye movement analysis apparatus comprising:
   imaging means including an imaging camera and a light source for projecting imaging light to an eyeball to image eye movements through such a quick exposure as not to blur an imaging object;
   image recording means for recording imaged outputs produced from said imaging camera of said imaging means;
   tracing destination specifying means for specifying the center of an eyeball and a position outside said center of said eyeball, said center of said eyeball and said position outside said center of said eyeball being designations for tracing imaged outputs produced from said imaging camera;
   position coordinate calculating means for calculating position coordinates of said center of said eyeball and said position outside said center of said eyeball specified by said tracing destination specifying means for each single piece of image data sequentially read from said image recording means; and
   eye movement calculating means for calculating an eye movement incorporating a torsional component from time-dependent changes in position coordinates of said center of said eyeball and said position outside said center of said eyeball obtained from said position coordinate calculating means, wherein polarizing plates are disposed in front of an optical lens of said imaging camera and in front of said light source and quarter-wave plates are disposed in front of said polarizing plates.

3. An eye movement analysis apparatus comprising:
   imaging means including an imaging camera and a light source for projecting imaging light to an eyeball to image eye movements through such a quick exposure as not to blur an imaging object;
   image recording means for recording imaged outputs produced from said imaging camera of said imaging means;
   tracing destination specifying means for specifying the center of an eyeball and a position outside said center of said eyeball, said center of said eyeball and said position outside said center of said eyeball being designations for tracing imaged outputs produced from said imaging camera;
   position coordinate calculating means for calculating position coordinates of said center of said eyeball and said position outside said center of said eyeball specified by said tracing destination specifying means for each single piece of image data sequentially read from said image recording means; and
   eye movement calculating means for calculating an eye movement incorporating a torsional component from time-dependent changes in position coordinates of said center of said eyeball and said position outside said center of said eyeball obtained from said position coordinate calculating means, wherein a light-transmitting light-scattering member is dispersed in front of said light source.

4. An eye movement analysis apparatus comprising:
   imaging means including an imaging camera and a light source for projecting imaging light to an eyeball to image eye movements through such a quick exposure as not to blur an imaging object;
   image recording means for recording imaged outputs produced from said imaging camera of said imaging means;
   tracing destination specifying means for specifying the center of an eyeball and a position outside said center of said eyeball, said center of said eyeball and said position outside said center of said eyeball being designations for tracing imaged outputs produced from said imaging camera;
   position coordinate calculating means for calculating position coordinates of said center of said eyeball and said position outside said center of said eyeball specified by said tracing destination specifying means for each single piece of image data sequentially read from said image recording means; and
   eye movement calculating means for calculating an eye movement incorporating a torsional component from time-dependent changes in position coordinates of said center of said eyeball and said position outside said center of said eyeball obtained from said position coordinate calculating means, wherein said light source is oriented opposite to an eyeball; a light reflecting board is disposed to as to confront said light source; and cylindrical light reflecting board is disposed around said light source.

5. An eye movement analysis apparatus comprising:
imaging means including an imaging camera and a light source for projecting imaging light to an eyeball to image eye movements through such a quick exposure as not to blur an imaging object;
image recording means for recording imaged outputs produced from said imaging camera of said imaging means;
tracing destination specifying means for specifying the center of an eyeball and a position outside said center of said eyeball, said center of said eyeball and said position outside said center of said eyeball being designations for tracing imaged outputs produced from said imaging camera;
position coordinate calculating means for calculating position coordinates of said center of said eyeball and said position outside said center of said eyeball specified by said tracing destination specifying means for each single piece of image data sequentially read from said image recording means; and
eye movement calculating means for calculating an eye movement incorporating a torsional component from time-dependent changes in position coordinates of said center of said eyeball and said position outside said center of said eyeball obtained from said position coordinate calculating means, wherein a light-emitting diode is used as said light source, and when lighting said light-emitting diode for a short duration to perform said quick exposure, said light-emitting diode is reverse-biased.

6. An eye movement analysis apparatus comprising:
imaging means including an imaging camera and a light source for projecting imaging light to an eyeball to image eye movements through such a quick exposure as not to blur an imaging object;
image recording means for recording imaged outputs produced from said imaging camera of said imaging means;
tracing destination specifying means for specifying the center of an eyeball and a position outside said center of said eyeball, said center of said eyeball and said position outside said center of said eyeball being designations for tracing imaged outputs produced from said imaging camera;
position coordinate calculating means for calculating position coordinates of said center of said eyeball and said position outside said center of said eyeball specified by said tracing destination specifying means for each single piece of image data sequentially read from said image recording means; and
eye movement calculating means for calculating an eye movement incorporating a torsional component from time-dependent changes in position coordinates of said center of said eyeball and said position outside said center of said eyeball obtained from said position coordinate calculating means, wherein a light-emitting diode is used as said light source, and when lighting said light-emitting diode for a short duration to perform said quick exposure, the anode of said light-emitting diode is grounded in synchronism with a falling edge of a light-emitting pulse signal supplied to said light-emitting diode.

7. An eye movement analysis method comprising the steps of:
(a) imaging eye movements of an eyeball of a subject by video recording means using a reverse-biased light—emitting diode as a light source, and lighting said diode for short duration to perform a quick exposure;
(b) appending a time code to each video signal recorded in step (a);
(c) recording the time coded video signals obtained by step (b) in video tape recorder means;
(d) entering a desired number of frames (n) to be analyzed from a keyboard;
(e) reproducing the image data signals recorded in step (c), and maintaining said image data signal of a first frame until a frame forwarding signal is supplied from a control circuit section;
(f) converting said image data signal reproduced in step (e) into a digital signal;
(g) storing said digital signal obtained in step (f) into a frame buffer;
(h) setting a window to each eyeball center and a position outside said eyeball center of said image data signal of said first frame;
(i) reading said digital signal from said frame buffer in step (g) and converting said data into binary coded data of luminance data corresponding to a light level and a dark level;
(j) tracing said eyeball center and said position outside said eyeball center set in said window at step (h) using said image data obtained in step (i), and determining position coordinates of said eyeball center and said position outside said eyeball center;
(k) storing said position coordinates obtained by step (j) into a memory;
(l) determining position coordinates of said eyeball center and said position outside said eyeball center, and storing respective position coordinates into said memory from said first frame to the nth frame each time said frame forwarding signal is received; and
(m) calculating time-dependent vertical and horizontal changes and time-dependent torsional angle changes in said position coordinates of said eyeball center and said position outside said eyeball center in accordance with said position coordinates of said eyeball center and said position outside said eyeball center from said first frame to nth frame and said time code appended to each video signal recorded in step (b).

* * * * *